United States Patent
Nair et al.

(10) Patent No.: US 10,035,743 B1
(45) Date of Patent: Jul. 31, 2018

(54) METHOD FOR CONVERSION OF 1, 3, 3, 3-TETRAFLUOROPROPENE (HFO-1234ZE) TO 1-CHLORO-3, 3, 3-TRIFLUOROPROPENE (HCFO-1233ZD)

(71) Applicant: Honeywell International inc., Morris Plains, NJ (US)

(72) Inventors: Haridasan K. Nair, Williamsville, NY (US); Rajiv Ratna Singh, Getzville, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/797,015

(22) Filed: Oct. 30, 2017

(51) Int. Cl.
| | |
|---|---|
| *C07C 17/087* | (2006.01) |
| *C07C 17/20* | (2006.01) |
| *C07C 21/18* | (2006.01) |
| *B01J 27/128* | (2006.01) |
| *C07C 19/08* | (2006.01) |
| *B01J 27/10* | (2006.01) |
| *C07C 17/25* | (2006.01) |

(52) U.S. Cl.
CPC ............. *C07C 17/087* (2013.01); *B01J 27/10* (2013.01); *B01J 27/128* (2013.01); *C07C 17/206* (2013.01); *C07C 17/208* (2013.01); *C07C 17/25* (2013.01); *C07C 19/08* (2013.01); *C07C 21/18* (2013.01)

(58) Field of Classification Search
CPC ........................... C07C 17/087; C07C 17/206
See application file for complete search history.

(56) References Cited

U.S. PATENT DOCUMENTS

| | | |
|---|---|---|
| 9,556,091 B2 | 1/2017 | Cottrell et al. |
| 2014/0005447 A1 | 1/2014 | Okamoto et al. |

*Primary Examiner* — Medhanit W Bahta
(74) *Attorney, Agent, or Firm* — Faegre Baker Daniels LLP

(57) ABSTRACT

A method for converting 1, 3, 3, 3-tetrafluoropropene (HFO-1234ze) to 1-chloro-3, 3, 3-trifluoropropene (HCFC-1233zd) with high selectivity and without significant formation of 1, 1, 1, 3, 3-pentafluoropropane (HFC-245fa), by reacting 1234ze and hydrogen chloride (HCl) in a gas phase using a ferric chloride ($FeCl_3$) catalyst or a ruthenium chloride ($RuCl_3$) catalyst.

20 Claims, No Drawings

METHOD FOR CONVERSION OF 1, 3, 3, 3-TETRAFLUOROPROPENE (HFO-1234ZE) TO 1-CHLORO-3, 3, 3-TRIFLUOROPROPENE (HCFO-1233ZD)

BACKGROUND

1. Field of the Disclosure

The present disclosure is related to a method for converting 1, 3, 3, 3-tetrafluoropropene (HFO-1234ze) to 1-chloro-3, 3, 3-trifluoropropene (HCFC-1233zd).

2. Description of the Related Art 1-chloro-3, 3, 3-trifluoropropene ($CF_3CH=CHCl$, HCFC-1233zd, or 1233zd) is a commercially important low global warming compound currently used for many applications, including as a foam blowing agent and aerosol propellant.

There are many known methods for the preparation of 1233zd, which typically employ the approach of reacting a suitable starting material with hydrogen fluoride (HF), for example as disclosed in U.S. Pat. No. 9,556,091. In U.S. Patent Application Publication No. 2014/0005447, the conversion of 1, 3, 3, 3-tetrafluoropropene (HFO-1234ze, or 1234zd) to 1233zd is disclosed, though disadvantageously, 1, 1, 1, 3, 3-pentafluoropropane (HFC-245fa, or 245fa) is produced as a by-product in significant amounts of from greater than 0.1 wt. % to about 10 wt. %, based on the overall product composition, using particular catalysts. The 245fa by-product is very difficult to separate from 1233zd by distillation, for example, due to the potential for 245fa to form an azeotrope with 1233zd.

What is needed is a method for conversion of 1234ze to 1233zd without significant formation of 245fa as a by-product.

SUMMARY

The present disclosure provides a method for converting 1, 3, 3, 3-tetrafluoropropene (HFO-1234ze) to 1-chloro-3, 3, 3-trifluoropropene (HCFC-1233zd) with high selectivity and without significant formation of 1, 1, 1, 3, 3-pentafluoropropane (HFC-245fa), by reacting 1234ze and hydrogen chloride (HCl) in a gas phase using a ferric chloride ($FeCl_3$) catalyst or a ruthenium chloride ($RuCl_3$) catalyst.

In one form thereof, the present disclosure provides a method for converting 1, 3, 3, 3-tetrafluoropropene (HFO-1234ze) to 1-chloro-3, 3, 3-trifluoropropene (HCFC-1233zd), comprising the step of reacting HFO-1234ze with hydrogen chloride (HCl) in a gas phase in the presence of a catalyst selected from the group consisting of ferric chloride ($FeCl_3$) and ruthenium chloride ($RuCl_3$) to form a product composition comprising HCFC-1233zd, the product composition including less than 0.15 area percent of 1, 1, 1, 3, 3-pentafluoropropane (HFC-245fa), based on the total area percent of the product composition as determined by gas chromatography (GC).

In one embodiment, the catalyst is ferric chloride ($FeCl_3$), and the product composition may include less than 0.1 area percent of 1, 1, 1, 3, 3-pentafluoropropane (HFC-245fa), based on the total area percent of the product composition, as determined by gas chromatography (GC). The product composition may alternatively include less than 0.05 area percent of 1, 1, 1, 3, 3-pentafluoropropane (HFC-245fa), based on the total area percent of the product composition, as determined by gas chromatography (GC). The product composition may alternatively include no detectable amount of 1, 1, 1, 3, 3-pentafluoropropane (HFC-245fa), based on the total area percent of the product composition, as determined by gas chromatography (GC).

In another embodiment, the catalyst is ruthenium chloride ($RuCl_3$), and the product composition may include less than 0.1 area percent of 1, 1, 1, 3, 3-pentafluoropropane (HFC-245fa), based on the total area percent of the product composition, as determined by gas chromatography (GC). The product composition may alternatively, include less than 0.05 area percent of 1, 1, 1, 3, 3-pentafluoropropane (HFC-245fa), based on the total area percent of the product composition, as determined by gas chromatography (GC). The product composition may alternatively include no detectable amount of 1, 1, 1, 3, 3-pentafluoropropane (HFC-245fa), based on the total area percent of the product composition as determined by gas chromatography (GC).

The reacting step may be carried out at a temperature between 250° C. and 400° C., or at a temperature between 275° C. and 350° C.

The reacting step may be carried out at a contact time of the HFO-1234ze and HCl to the catalyst of between 2 seconds and 30 seconds, or between 5 seconds and 20 seconds.

The reacting step may be conducted in a continuous manner. The reacting step may achieve a selectivity to HCFC-1233zd in the product composition of at least 95%.

In another form thereof, the present disclosure provides a method for converting 1, 3, 3, 3-tetrafluoropropene (HFO-1234ze) to 1-chloro-3, 3, 3-trifluoropropene (HCFC-1233zd), comprising the step of reacting HFO-1234ze with hydrogen chloride (HCl) in a gas phase in the presence of a ferric chloride ($FeCl_3$) catalyst at a temperature between 250° C. and 400° C. to form a product composition comprising HCFC-1233zd, the product composition including less than 0.1 area percent of 1, 1, 1, 3, 3-pentafluoropropane (HFC-245fa), based on the total area percent of the product composition as determined by gas chromatography (GC).

The product composition may include less than 0.05 area percent of 1, 1, 1, 3, 3-pentafluoropropane (HFC-245fa), based on the total area percent of the product composition, as determined by gas chromatography (GC), or the product composition may include no detectable amount of 1, 1, 1, 3, 3-pentafluoropropane (HFC-245fa), based on the total area percent of the product composition, as determined by gas chromatography (GC).

The reacting step may be carried out at a contact time of the HFO-1234ze and HCl to the catalyst of between 2 seconds and 30 seconds. The reacting step may achieve a selectivity to HCFC-1233zd in the product composition of at least 95%.

It is to be understood that both the foregoing general description and the following detailed description are exemplary and explanatory only and are not restrictive of the disclosure as claimed. Other embodiments will be apparent to those skilled in the art from consideration of the specification and practice of the disclosure disclosed herein.

DETAILED DESCRIPTION

The present disclosure provides a method for converting 1, 3, 3, 3-tetrafluoropropene (HFO-1234ze) to 1-chloro-3, 3, 3-trifluoropropene (HCFC-1233zd) with high selectivity and without significant formation of 1, 1, 1, 3, 3-pentafluoropropane (HFC-245fa), by reacting 1234ze and hydrogen chloride (HCl) in a gas phase using a ferric chloride (FeCl$_3$) catalyst or a ruthenium chloride (RuCl$_3$) catalyst.

Except as specifically set forth otherwise herein, the designations "HFO-1234ze" and "HCFC-1233zd" refer collectively to both the trans-(E) and the cis-(Z) isomers of the foregoing compounds.

The principal reaction of the present disclosure is set forth below as reaction (I):

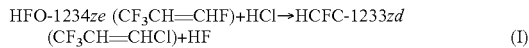

$$\text{HFO-1234}ze \; (\text{CF}_3\text{CH}=\text{CHF}) + \text{HCl} \rightarrow \text{HCFC-1233}zd \; (\text{CF}_3\text{CH}=\text{CHCl}) + \text{HF} \quad \text{(I)}$$

The reaction (I) may be conducted by exposing a mixture of HFO-1234ze and HCl in a gas phase to a catalyst, such as by passing a mixture of HFO-1234ze and HCl in a gas phase over a heated column of catalyst in a stainless steel tube reactor at elevated temperature. The ratio of HFO-1234ze to HCl in the reaction may be about 1:1, but can vary from 1:1 to 1:3, and may be 1:1, 1:2, or 1:3, for example.

In the present reaction, the HFO-1234ze in the reaction mixture may be substantially pure. In one embodiment, the HFO-1234ze may have a purity level of at least 90 wt. %, at least 95 wt. %, at least 98 wt. % or at least 99 wt. %, for example. The HCl in the reaction mixture may also be substantially pure, for example, the HCl may have a purity level of at least 90 wt. %, at least 95 wt. %, at least 98 wt. % or at least 99 wt. %, for example.

In one embodiment, the gas phase reaction composition includes substantially only HFO-1234ze and HCl, and any impurities, i.e., elements or compounds other than HFO-1234ze and HCl, if present, are present in an amount of less than 5 wt. %, less than 3 wt. %, less than 1 wt. %, or less than 0.5 wt. %, based on the total weight of the gas phase reaction composition.

The temperature in the reactor may be as low as 250° C., 275° C., 300° C., or 325° C., or may be as high as 375° C., 400° C., 425° C., or 450° C., or may be within any range defined between any two of the foregoing values, such as 250° C. to 450° C., 275° C. to 425° C., 300° C. to 400° C., or 325° C. to 375° C., for example.

The contact time between the HFO-1234ze and HCl mixture and the catalyst in the reactor, as regulated via suitable flow controls, may be as little as 2 seconds, 5 seconds, or 8 seconds, or may be as great as 12 seconds, 20 seconds, or 30 seconds, or more, or may be within any range defined between any two of the foregoing values, such as 2 seconds to 30 seconds, 5 seconds to 20 seconds, or 8 seconds to 12 seconds, for example.

The catalyst may be a metallic chloride catalyst, in particular ferric chloride (FeCl$_3$) or ruthenium chloride (RuCl$_3$) or, in a further embodiment, may be osmium chloride (OsCl$_3$).

The catalyst may be supported on carbon, such as activated carbon in the form of pellets of various shapes, as well as beads, spheres, or sieves, for example. In other embodiments, the catalyst may be supported on alumina and/or silica in the any of the foregoing forms.

In one embodiment, the catalyst is impregnated onto a carbon support at a weight percent of catalyst, as a percentage of the total weight of the catalyst and support, in an amount as low as 1 wt. %, 4 wt. %, or 6 wt. %, or as high as 8 wt. %, 10 wt. %, or 20 wt. %, or in an amount within any range defined between any pair of the foregoing values, such as 1 to 20 wt. %, 4 to 10 wt. %, or 6 to 8 wt. %, for example.

Suitable carbon supports are available from Calgon Carbon Corporation. The catalyst may also be a commercially available Weert catalyst (e.g., 4 wt. % FeCl$_3$/C). Impregnation of FeCl$_3$ or RuCl$_3$ on the support may be according to typical methods known in the art.

The reaction may be carried out in a batch manner or in a continuous manner. In a batch reaction or process, reactants are supplied to a reaction vessel and the reaction is allowed to proceed, following by removing the products. In a continuous reaction or process, reactants are continuously supplied, or periodically supplied, to a reaction vessel, and reactants are continuously removed, or periodically removed from the reaction vessel.

Advantageously, it has been found that the reaction forms only very minimized amounts of HFC-245fa, or even no detectable amount of HFC-245fa.

In the present reaction, HFC-245fa is formed as a by-product in amounts less than 0.15 area %, less than 0.10 area %, less than 0.075 area %, less than 0.05 area %, less than 0.025 area %, or less than 0.001 area %. Stated alternatively, HFC-245fa may be formed as a by-product of the present process in an amount as little as 0.001 area %, 0.025 area %, or 0.05 area %, or as great as 0.075 area %, 0.10 area %, or 0.15 area %, or within any range defined between any two of the foregoing values, such as 0.001 area % to 0.15 area %, 0.025 area % to 0.10 area %, or 0.05 area % to 0.075 area %, for example.

Further, in the present reaction, HFC-245fa is formed as a by-product in amounts less than 150 ppm, less than 125 ppm, less than 100 ppm, less than 75 ppm, less than 50 ppm, or less than 25 ppm.

The product composition may be collected from the reactor in a gas sample bags or via other means, and the amounts of the various components of the product composition, including any detected HFC-245fa, may be determined by gas chromatography (GC) and/or gas chromatography/mass spectroscopy (GC-MS).

Advantageously, the reaction is also highly selective to HCFC-1233zd and may achieve a selectivity to HCFC-1233zd of as little as 90%, 92%, or 95%, or as great as 98%, 99%, or 99.5%, or within any range defined between any pair of the foregoing values, such as 90% to 99.5%, 92% to 99%, or 95% to 98%, for example.

Conversion of HFO-1234ze to HCFC-1233zd may be influenced by the reaction temperature and/or the HFO-1234ze/HCl reactant ratio wherein, as set forth below in Example 1, relatively higher temperatures and an increase in HCl in the HFO-1234ze/HCl reactant ratio tend to result in increased conversion. However, the results of Example 1 below may also be optimized based on the teachings presented herein.

EXAMPLES

Example 1

Conversion of HFO-1234ze to HCFC-1233zd

Appropriate catalyst (10 cm$^3$) was loaded into a 0.5" diameter×12" length Monel tube reactor. The catalyst was held in place by stainless steel wool on both ends of the catalyst column inside the reactor. The reactants HFO-1234ze and HCl in gas phase were continuously fed into the reactor through suitable mass flow controllers the rate of which can be adjusted as per experimental requirements. The tube was placed in a furnace where it was heated and maintained at the desired temperature. Exit gases were periodically collected in Tedlar® bags or in a cold (−78° C.) stainless steel cylinder (~100-200 cm$^3$ volume) for GC and GC-MS analyses. All experiments were conducted with a molar ratio of 1:1 for the reactants unless indicated otherwise below.

Experimental conditions and product distributions are summarized in Table 1 below.

TABLE 1

| Expt. | **Reaction conditions | | | Products -GC area % | | | | | | 1233zd |
|---|---|---|---|---|---|---|---|---|---|---|
| | | | | 1234ze | | 1233zd | | by-products | | (trans + cis) |
| No # | *Type of Catalyst | Temp. in ° C. | CT sec in sec | Trans % | Cis % | Trans % | Cis % | 245fa % | Others % | Selectivity % |
| 1 | F-Al$_2$O$_3$ | 350 | 15 | 55.92 | 12.79 | 24.64 | 3.66 | 2.36 | 0.63 | 80.9 |
| 2 | F-Al$_2$O$_3$ | 350 | 10 | 49.91 | 10.6 | 33.21 | 4.88 | 1.28 | 0.12 | 92.9 |
| 3 | F-Cr$_2$O$_3$ | 350 | 10 | 40.7 | 8.42 | 40.1 | 6.1 | 1.65 | 3.03 | 81.6 |
| 4 | F-Cr$_2$O$_3$ | 300 | 10 | 47.33 | 9.43 | 35.31 | 4.89 | 2.55 | 0.49 | 85.9 |
| 5 | FeCl$_3$/C (Weert) | 350 | 10 | 24.42 | 2.97 | 61.62 | 10.06 | 0.04 | 0.89 | 97.4 |
| 6 | FeCl$_3$/C (Weert) | 300 | 10 | 48.88 | 4.86 | 40.21 | 5.8 | 0.04 | 0.21 | 98.9 |
| 7 | FeCl$_3$/C (Weert) | 350 | 15 | 33.25 | 6.02 | 52.35 | 8.17 | 0.04 | 0.17 | 99.3 |
| 8 | FeCl$_3$/C (Weert) | 350 | 15 | 58.69 | 4.91 | 29.44 | 4 | 0 | 2.96 | 83.7 |
| 9 | FeCl$_3$/C (Calgon) | 350 | 20 | 48.48 | 7.2 | 38.48 | 5.74 | 0 | 0.1 | 99.5 |
| 10 | FeCl$_3$/C (Calgon) | 275 | 10 | 93 | 2.11 | 4.42 | 0.4 | 0 | 0.07 | 97.1 |
| 11 | FeCl$_3$/C (Calgon) | 275 | 15 | 95.37 | 1.39 | 2.78 | 0.38 | 0 | 0.08 | 95.1 |
| 12 | FeCl$_3$/Calgon*** | 275 | 5 | 45 | 4 | 43.99 | 6.27 | 0 | 0.1 | 98.4 |
| 13 | FeCl$_3$/Calgon*** | 300 | 5 | 40.16 | 3.76 | 48.99 | 6.27 | 0 | 0.28 | 98.0 |
| 14 | FeCl$_3$/C (Weert) | 275 | 15 | 74.37 | 4.2 | 19.2 | 1.91 | 0 | 0.32 | 97.0 |
| 15 | FeCl$_3$/C (Weert) | 275 | 30 | 65.39 | 4.71 | 27.07 | 2.6 | 0.01 | 0.22 | 98.5 |
| 16 | RuCl$_3$/C | 350 | 15 | 95.45 | 2.83 | 1.22 | 0.21 | 0 | 0.29 | 66.3 |

*F-Al$_2$O$_3$ (gama alumina)
Calgon = Calgon carbon pellets, FeCl$_3$ and RuCl$_3$ (~10 wt. % impregnated on Calgon carbon pellets)
FeCl$_3$ (Weert ~4% FeCl$_3$ on carbon-commercial product)
**Ratios 1234ze:HCl were 1:1 unless noted otherwise
***Ratios of 1234ze to HCl were 1:2 and 1:1.6 for expts. 12 and 13, respectively.

As can be seen from the results in Table 1 above, reactions 5-15 catalyzed by the ferric chloride (FeCl$_3$) catalyst and reaction 16 catalyzed by the ruthenium chloride (RuCl$_3$) catalyst produced the least amount of 245fa as a by-product, with reactions 8-12 producing no detectable 245fa. By contrast, reactions 1-4 catalyzed by the fluorinated chromia or alumina catalysts could not completely avoid the formation of 245fa, and produced 245fa in amounts of 3.66 GC area % or greater. Although the reactant ratios of HFO-1234ze and HCl used in the Example were 1:1, it was found that increasing the ratio to 1:2 in reaction 12 and to 1:1.6 in reaction 13 increased the conversion but not the selectivity.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

The invention claimed is:

1. A method for converting 1,3,3,3-tetrafluoropropene (HFO-1234ze) to 1-chloro-3,3,3-trifluoropropene (HCFC-1233zd), comprising the step of:
reacting HFO-1234ze with hydrogen chloride (HCl) in a gas phase in the presence of a catalyst selected from the group consisting of ferric chloride (FeCl$_3$) and ruthenium chloride (RuCl$_3$) to form a product composition comprising HCFC-1233zd, the product composition including less than 0.05 area percent of 1,1,1,3,3-pentafluoropropane (HFC-245fa), based on the total area percent of the product composition as determined by gas chromatography (GC).

2. The method of claim 1, wherein the catalyst is ferric chloride (FeCl$_3$).

3. The method of claim 2, wherein the product composition includes less than 0.001 area percent of 1,1,1,3,3-pentafluoropropane (HFC-245fa), based on the total area percent of the product composition, as determined by gas chromatography (GC).

4. The method of claim 2, wherein the product composition includes no detectable amount of 1,1,1,3,3-pentafluoropropane (HFC-245fa), based on the total area percent of the product composition, as determined by gas chromatography (GC).

5. The method of claim 1, wherein the catalyst is ruthenium chloride (RuCl$_3$).

6. The method of claim 5, wherein the product composition includes less than 0.025 area percent of 1,1,1,3,3-pentafluoropropane (HFC-245fa), based on the total area percent of the product composition, as determined by gas chromatography (GC).

7. The method of claim 5, wherein the product composition includes less than 0.001 area percent of 1,1,1,3,3-pentafluoropropane (HFC-245fa), based on the total area percent of the product composition, as determined by gas chromatography (GC).

8. The method of claim 5, wherein the product composition includes no detectable amount of 1,1,1,3,3-pentafluoropropane (HFC-245fa), based on the total area percent of the product composition as determined by gas chromatography (GC).

9. The method of claim 1, wherein the reacting step is carried out at a temperature between 250° C. and 400° C.

10. The method of claim 1, wherein the reacting step is carried out at a temperature between 275° C. and 350° C.

11. The method of claim 1, wherein the reacting step is carried out at a contact time of the HFO-1234ze and HCl to the catalyst of between 2 seconds and 30 seconds.

12. The method of claim 1, wherein the reacting step is carried out at a contact time of the HFO-1234ze and HCl to the catalyst of between 5 seconds and 20 seconds.

13. The method of claim 1, wherein the reacting step is conducted in a continuous manner.

14. The method of claim 1, wherein the reacting step achieves a selectivity to HCFC-1233zd in the product composition of at least 95%.

15. A method for converting 1,3,3,3-tetrafluoropropene (HFO-1234ze) to 1-chloro-3,3,3-trifluoropropene (HCFC-1233zd), comprising the step of:

reacting HFO-1234ze with hydrogen chloride (HCl) in a gas phase in the presence of a ferric chloride (FeCl$_3$) catalyst at a temperature between 250° C. and 400° C. to form a product composition comprising HCFC-1233zd, the product composition including less than 0.05 area percent of 1,1,1,3,3-pentafluoropropane (HFC-245fa), based on the total area percent of the product composition as determined by gas chromatography (GC).

16. The method of claim 15, wherein the product composition includes less than 0.001 area percent of 1,1,1,3,3-pentafluoropropane (HFC-245fa), based on the total area percent of the product composition, as determined by gas chromatography (GC).

17. The method of claim 15, wherein the product composition includes no detectable amount of 1,1,1,3,3-pentafluoropropane (HFC-245fa), based on the total area percent of the product composition, as determined by gas chromatography (GC).

18. The method of claim 15, wherein the reacting step is carried out at a contact time of the HFO-1234ze and HCl to the catalyst of between 2 seconds and 30 seconds.

19. The method of claim 15, wherein the reacting step achieves a selectivity to HCFC-1233zd in the product composition of at least 95%.

20. A method for converting 1,3,3,3-tetrafluoropropene (HFO-1234ze) to 1-chloro-3,3,3-trifluoropropene (HCFC-1233zd), comprising the step of:

reacting HFO-1234ze with hydrogen chloride (HCl) in a gas phase in the presence of a catalyst selected from the group consisting of ferric chloride (FeCl$_3$) and ruthenium chloride (RuCl$_3$) to form a product composition comprising HCFC-1233zd, the product composition not including 1,1,1,3,3-pentafluoropropane (HFC-245fa).

* * * * *